(12) United States Patent
Wada

(10) Patent No.: US 7,820,004 B2
(45) Date of Patent: Oct. 26, 2010

(54) METHOD FOR PRODUCING WORN ARTICLE

(75) Inventor: Takao Wada, Osaka (JP)

(73) Assignee: Zuiko Corporation, Osaka (JP)

( * ) Notice: Subject to any disclaimer, the term of this patent is extended or adjusted under 35 U.S.C. 154(b) by 344 days.

(21) Appl. No.: 12/090,376

(22) PCT Filed: Dec. 5, 2006

(86) PCT No.: PCT/JP2006/324234

§ 371 (c)(1),
(2), (4) Date: Apr. 16, 2008

(87) PCT Pub. No.: WO2007/069496

PCT Pub. Date: Jun. 21, 2007

(65) Prior Publication Data

US 2009/0165941 A1    Jul. 2, 2009

(30) Foreign Application Priority Data

Dec. 16, 2005  (JP) .............................. 2005-363481

(51) Int. Cl.
*B32B 37/00* (2006.01)
(52) U.S. Cl. .................. 156/259; 156/271; 156/161; 156/229; 156/302
(58) Field of Classification Search .................. 156/271, 156/259, 161, 229, 302
See application file for complete search history.

(56) References Cited

U.S. PATENT DOCUMENTS 5,858,151 A    1/1999    Igaue et al.
7,419,562 B2 *    9/2008    Van Gompel et al. ....... 156/259
2002/0151864 A1    10/2002    Otsubo et al.

FOREIGN PATENT DOCUMENTS

| EP | 1 661 535 | 5/2006 |
|---|---|---|
| JP | 9-224973 | 9/1997 |
| JP | 2002-306534 | 10/2002 |
| JP | 2003-102777 | 4/2003 |
| JP | 2004-229978 | 8/2004 |
| WO | 2005/013871 | 2/2005 |

OTHER PUBLICATIONS

International Search Report for corresponding Application No. PCT/JP2006/324234 dated Dec. 26, 2006.

* cited by examiner

*Primary Examiner*—Linda L Gray
(74) *Attorney, Agent, or Firm*—Renner, Otto, Boisselle & Sklar, LLP

(57) ABSTRACT

A method for producing a worn article, capable of providing a desirable wearability while reducing the cost of production. The method includes the steps of: placing leg elastic members F along a first waveform $\alpha$ on a web W being carried, the first waveform $\alpha$ being continuous in a longitudinal direction L of the web W and having a predetermined wavelength $\lambda$ and predetermined first amplitudes $\alpha 1$ and $\alpha 2$, thereby producing a composite sheet Ws; and cutting off the composite sheet Ws being carried, along a cut-off line CL having a second waveform $\beta$ being continuous in the longitudinal direction L of the composite sheet Ws, having a wavelength $\lambda$ equal to the wavelength $\lambda$ and second amplitudes $\beta 1$ and $\beta 2$ smaller than the first amplitudes $\alpha 1$ and $\alpha 2$, and being in synchronism with the first waveform $\alpha$.

4 Claims, 4 Drawing Sheets

METHOD FOR PRODUCING WORN ARTICLE

TECHNICAL FIELD

The present invention relates to a method for producing worn articles such as disposable diapers and pants.

BACKGROUND ART

For processing worn articles, there has been proposed a processing method in which a continuous web is cut along a sine-curve pattern into a pair of separate webs, whose phases are then shifted from each other so that the protruding portions of the webs are bonded together. With this processing method, it is possible to avoid wastefully discarding cut-out pieces of the continuous web in the leg hole portions (for example, Japanese Laid-Open Patent Publication No. 9-224973 (FIG. 1, FIG. 3)).

With the conventional method, a pair of elastic members are placed on the continuous web in a sine-curve pattern and generally in parallel to each other, and the continuous web is cut off between the elastic members. Each of the separated webs includes a continuous elastic member placed thereon forming a shape conforming to leg holes.

DISCLOSURE OF THE INVENTION

With the conventional method, however, the elastic members are placed even in the protruding portions of the web where absorbent bodies are to be placed. Therefore, the absorbent body shrinks in the width direction around the crotch of the wearer due to the shrinkage of the elastic members, thereby causing a stiff feel. Thus, the wearability of the worn article lowers significantly.

Moreover, creases are more likely to occur during the carrying step after the cutting due to the shrinkage of the elastic members, thus making difficult the placement and bonding of absorbent bodies.

Furthermore, unnecessary elastic members are placed in the protruding portions, thus increasing the amount of elastic member to be used and hence the cost.

Thus, a primary object of the present invention is to provide a method for producing a worn article, capable of providing a desirable wearability while reducing the cost of production.

A worn article production method of the present invention is a method for producing a worn article, including a first torso portion covering a part of a torso of a wearer, a second torso portion covering another portion of the torso of the wearer, and a core portion covering a crotch of the wearer, the method including the steps of: carrying a strip-shaped web being continuous in a carrying direction and having a first side edge portion and a second side edge portion; placing a leg elastic member along a first waveform on the web being carried, the first waveform being continuous in a longitudinal direction of the web and having a predetermined wavelength and a predetermined first amplitude, thereby producing a composite sheet; cutting off the composite sheet being carried, along a cut-off line having a second waveform being continuous in the longitudinal direction of the composite sheet, having a wavelength equal to the predetermined wavelength and a second amplitude smaller than the first amplitude, and being in synchronism with the first waveform, thereby dividing the composite sheet into a first separate sheet including the first side edge portion and having first depressed portions and first protruding portions alternating each other along the cut-off line and a second separate sheet including the second side edge portion and having second protruding portions and second depressed portions alternating each other along the cut-off line, and cutting off the elastic member; shifting a phase of the first separate sheet and a phase of the second separate sheet from each other in a flow direction so that the first protruding portion and the second protruding portion faces each other; and placing the core portion so as to bridge between the first protruding portion and the second protruding portion.

According to this method, the amplitude of the second waveform forming the cut-off line of the composite sheet is smaller than that of the first waveform in which the elastic member is placed, whereby no elastic member is placed in the tip portion of each protruding portion. Thus, the leg elastic member is not placed in an area where the absorbent body is to be placed, thereby preventing the absorbent body from being deformed due to the shrinkage of the elastic member. Therefore, there will be no stiff feel of the absorbent body, thus significantly improving the wearability of the worn article.

Moreover, since no elastic member is placed in the tip portion of each protruding portion of each separate sheet, i.e., since no elastic member is placed in an area where the absorbent body is to be placed, the protruding portion will not be creased during the carrying step. Therefore, it is possible to easily and firmly place and bond the absorbent body to each separate sheet.

Furthermore, since no elastic member is placed in the tip portion of each protruding portion corresponding to the crotch of the wearer, the amount of elastic member to be used is reduced, thus realizing a significant cost reduction, as compared with a conventional method in which elastic members are placed on each separate sheet.

The term "worn article" as used herein refers to a concept including semi-finished products and finished products of disposable worn articles such as disposable diapers and pants.

In a preferred embodiment of the production method, the method may further include a step of relatively moving (increasing the interval between) the two separate sheets in a width direction perpendicular to the longitudinal direction so as to increase a width from the first side edge portion to the second side edge portion.

In a preferred embodiment of the production method, the relative movement may be performed so that the first protruding portion and the second protruding portion partially overlap with each other. In such an embodiment, it is easier to form leg holes conforming to legs.

DESCRIPTION OF THE REFERENCE NUMERALS

Figure 1A:
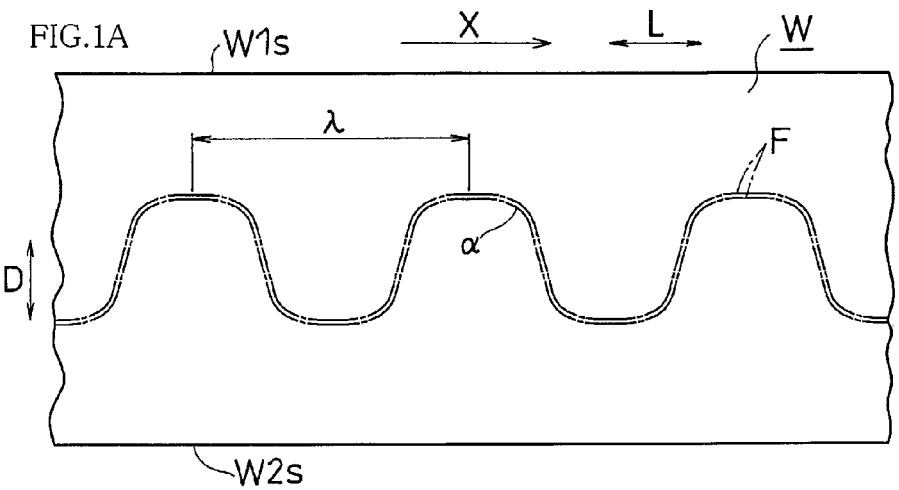
FIGS. 1A, 1B and 1C are schematic plan views each showing a part of an exemplary process of producing worn articles according to the present invention.

α: First waveform
α1, α2: First amplitude
β: Second waveform
β1, β2: Second amplitude
C: Core portion
CL: Cut-off line
D: Width direction
L: Longitudinal direction
S1: First torso portion
S2: Second torso portion
W: Web
W1: First separate sheet
W2: Second separate sheet
W1d: First depressed portion
W1u: First protruding portion
W2d: Second depressed portion
W2u: Second protruding portion
Ws: Composite sheet
W1s: First side edge portion
W2s: Second side edge portion
X: Carrying direction
λ: Wavelength

BEST MODE FOR CARRYING OUT THE INVENTION

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiment 1

One embodiment of the present invention will now be described with reference to the drawings.

Figure 3A:
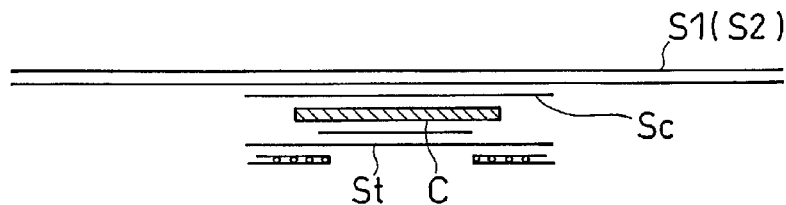
FIG. 3A is a schematic cross-sectional view showing an example of a worn article produced by the present production method.
Figure 3B:
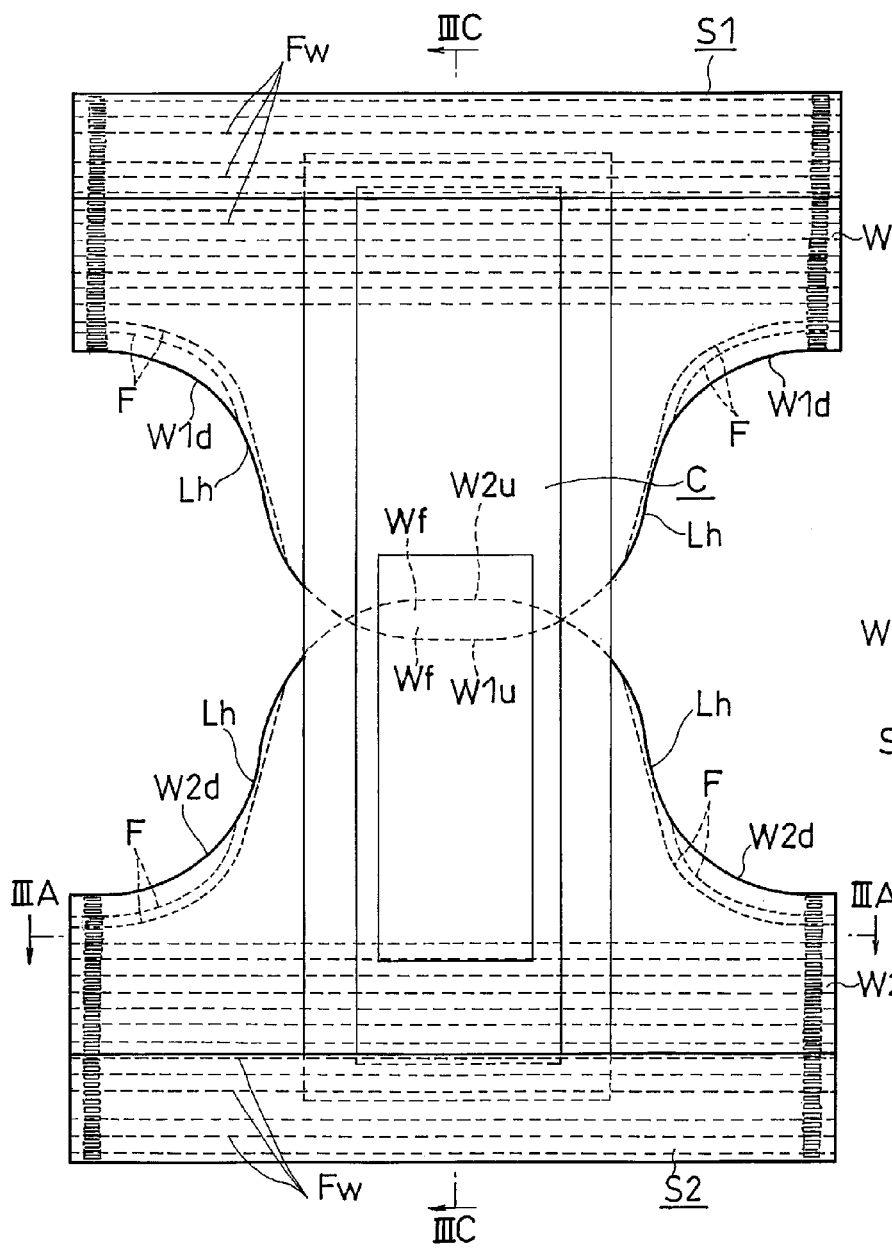
FIG. 3B is a schematic plan view thereof.
Figure 3C:
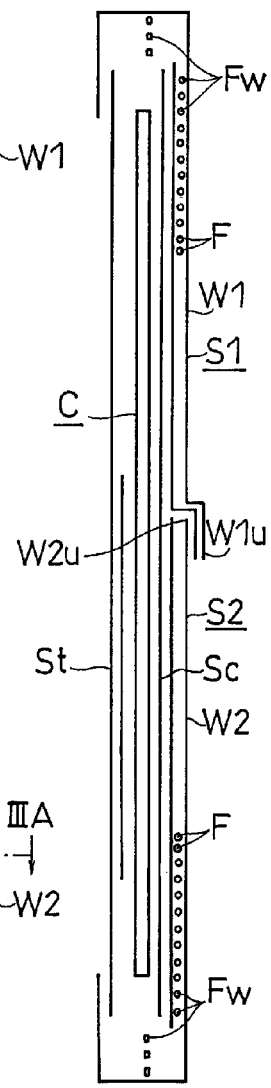
FIG. 3C is a schematic side view thereof.

FIGS. 3A, 3B and 3C show an example of a worn article produced by the present production method. As shown in FIGS. 3A, 3B and 3C, the worn article is formed in an "hourglass" shape including first and second torso portions S1 and S2 and a core portion C.

Leg elastic members F are placed along an outline of the first and second torso portions S1 and S2 forming leg hole portions Lh. The leg elastic members F are provided so that the leg hole portions Lh of the worn article will fit to the legs. The leg elastic members F are not placed in tip portions Wf of first and second protruding portions W1u and W2u protruding toward the center from the first and second torso portions S1 and S2 where the core portion C is placed.

Production Method:

An example of a method for producing a worn article will now be described.

Step of Producing Composite Sheet Ws:

As shown in FIG. 1A, a strip-shaped web W continuous in the carrying direction X has first and second side edge portions W1s and W2s. The web W is carried in the carrying direction X. One or more leg elastic members F are placed in a waveform pattern on the web W being carried, thus forming a composite sheet Ws. The composite sheet Ws may be formed with the elastic members F being interposed between a pair of webs W and W. The elastic members F are placed to be continuous in the longitudinal direction L of the web W. The elastic members F are placed generally in the central portion of the web W in the width direction D along the first waveform α having a predetermined wavelength λ.

Figure 1B:
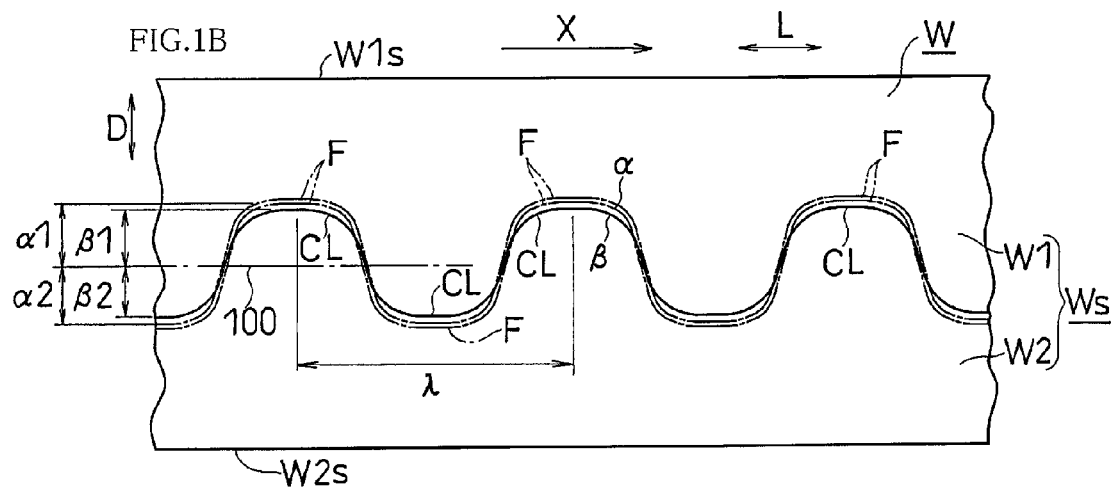

Division Step:

As shown in FIG. 1B, the composite sheet Ws being carried is cut off along the cut-off line CL continuous in the longitudinal direction L of the composite sheet Ws. As the composite sheet Ws is cut off, the composite sheet Ws is divided into first and second separate sheets W1 and W2.

The cut-off line CL is along the second waveform β continuous in the longitudinal direction L of the composite sheet Ws. The second waveform β has a wavelength equal to the wavelength λ of the first waveform α, and has the second amplitudes β1 and β2 smaller than the amplitudes α1 and α2 of the first waveform α. The second waveform β is in such a pattern as to extend in the longitudinal direction while moving in the width direction D of the composite sheet Ws in synchronism with the first waveform α. Specifically, in an area where the first waveform α changes closer to the first side edge portion W1s, the second waveform β also changes closer to the first side edge portion W1s, whereas in an area where the first waveform α changes closer to the second side edge portion W2s, the second waveform β also changes closer to the second side edge portion W2s.

The two waveforms α and β move in the width direction D in synchronism with each other, and are therefore close to each other. The elastic members F intersect with the cut-off line CL near a center line 100 of the composite sheet Ws, and the elastic members F are positioned slightly closer to the first side edge portion W1 than the cut-off line CL in the first separate sheet W1 and slightly closer to the second side edge portion W2s than the cut-off line CL in the second separate sheet W2.

Because of the positional relationship and shapes of the cut-off line CL and the elastic members F as described above, the elastic members F of FIG. 3B are placed along the leg holes Lh in opposite end portions of the worn article in the width direction while being absent in the width direction of the crotch.

Figure 1C:
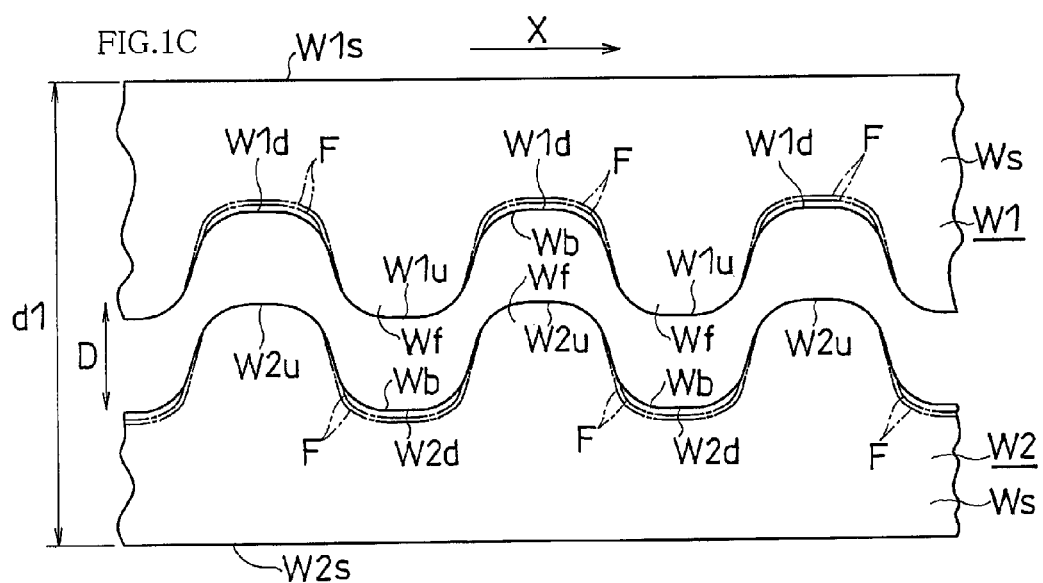

Interval-Increasing Step:

After the division described above, the process relatively moves (increases the interval between) the two separate sheets W1 and W2 in the width direction D so as to increase the width d1 from the first side edge portion W1s to the second side edge portion W2s, as shown in FIG. 1C.

The first separate sheet W1 includes the first side edge portion W1s, and has the first protruding portions W1u and first depressed portions W1d alternating each other along the cut-off line CL.

The second separate sheet W2 includes the second side edge portion W2s, and has second depressed portions W2d and the second protruding portions W2u alternating each other in the cut-off line CL.

As shown in FIG. 1B, the first amplitudes α1 and α2 of the first waveform a of the elastic members F are greater than the second amplitudes β1 and β2 of the second waveform B of the cut-off line CL. The shape and position of the cut-off line CL are determined so that the elastic members F are included in the depressed portions W1d and W2d of FIG. 1C but are not included in the tip portions Wf of the protruding portions W1u and W2u.

Thus, the elastic members F of the composite sheet Ws are divided along the cut-off line CL so that the elastic members F are included in trough portions W1b of the depressed portions W1d and W2d but are not included in the tip portions Wf of the protruding portions W1u and W2u. In other words, the elastic members F are cut off so that when a worn article is produced as shown in FIG. 3B, the absorbent body C and the leg elastic members F do not at all overlap with each other or overlap only slightly in the end portions of the absorbent body C in the width direction.

In the first and second waveforms α and β of FIG. 1B, the crest-side amplitudes α1 and β1 do not have to be equal to the trough-side amplitudes α2 and β2. It is only required that the first amplitudes α1 and α2 of the first waveform α are greater than the second amplitudes β1 and β2 of the second waveform β, and the first waveform α and the second waveform β are in synchronism with each other.

The interval between the separate sheets W1 and W2 can be increased as shown in FIG. 1C by increasing the distance d1 from the side edge portion W1s (W2s) of one separate sheet W1 (W2) to the side edge portion W2s (W1s) of the other separate sheet W2 (W1). For example, the interval between the separate sheets W1 and W2 may be increased so that they will later partially overlap with each other as shown in FIG. 2A.

Figure 2A:
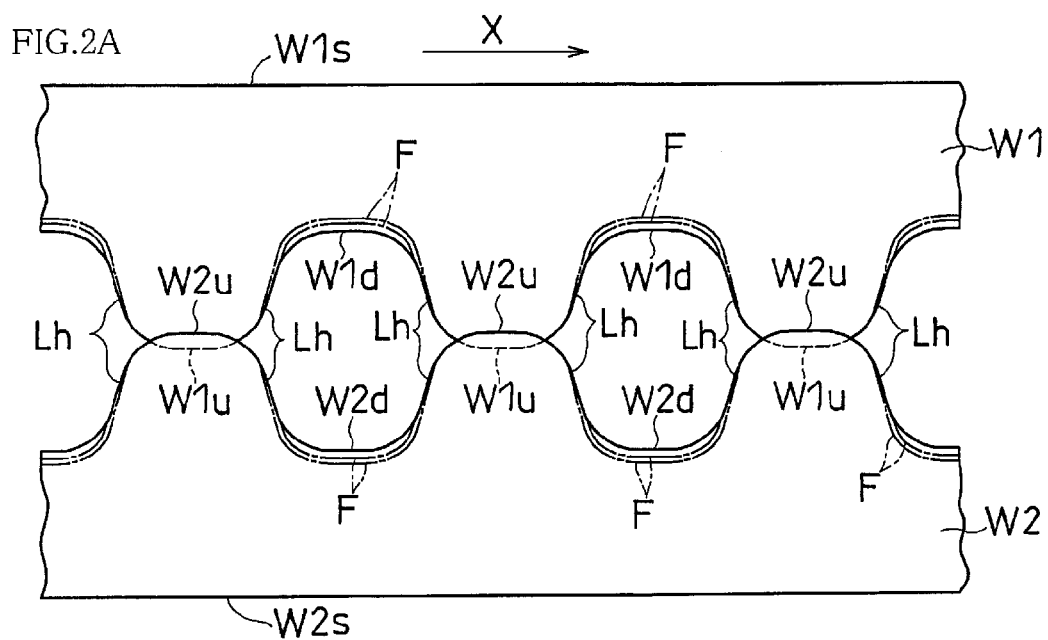
FIGS. 2A and 2B are schematic plan views each showing a part of the exemplary process of producing worn articles.

Phase Shifting Step:

Then, the phase of the first separate sheet W1 and that of the second separate sheet W2 are shifted from each other in the flow direction X so that the first protruding portion W1u and the second protruding portion W2u face each other, as shown in FIG. 2A. Specifically, the phase of one separate sheet W1 (W2) in the flow direction X is shifted by half a wavelength λ/2 from that of the other separate sheet W2 (W1). Then, the separate sheets W1 and W2 are carried with their protruding portions W1u and W2u facing each other and their depressed portions W1d and W2d facing each other. As a result of such a change in the phase, the separate sheets W1 and W2 are carried while being generally in line symmetry with each other with respect to the carrying direction X, with the separate sheets W1 and W2 forming the leg holes Lh.

The method for shifting the phases of the separate sheets W1 and W2 may be a method in which one separate sheet W1 (W2) is passed over a dummy roll, thus delaying the separate sheet W1 (W2) from the other separate sheet W2 (W1).

Figure 2B:
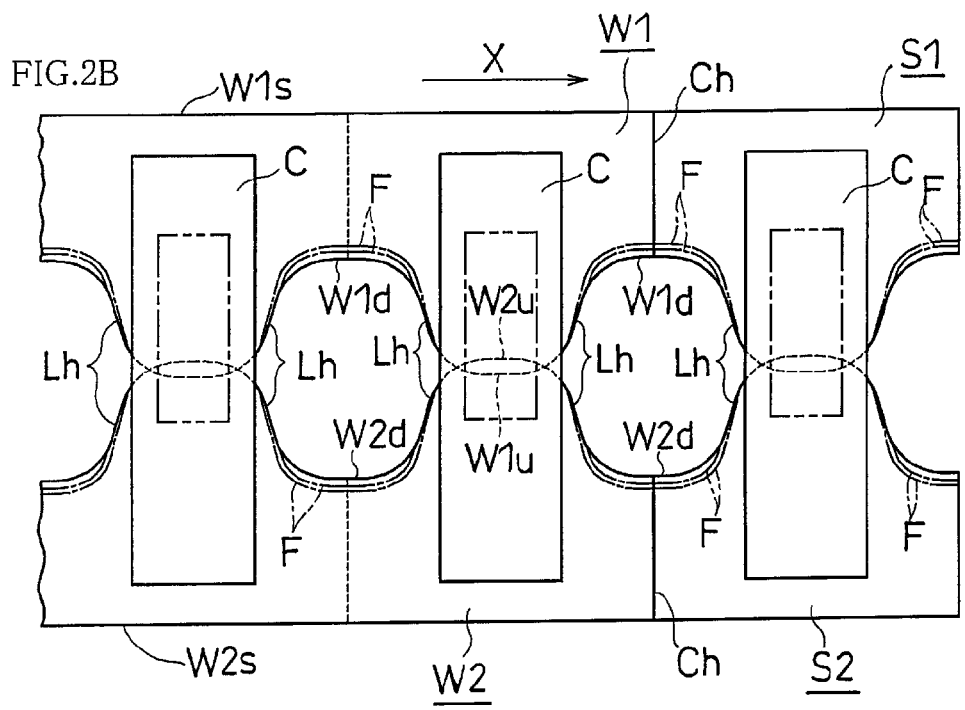

Then, as shown in FIG. 2B, the core portion C is placed on the separate sheets W1 and W2, after which the separate sheets W1 and W2 are carried downstream to be cut off along the cut-off line Ch into individual pairs of pants. Folding may be performed before the cutting so that the separate sheets W1 and W2 are laid on each other.

FIGS. 3A, 3B and 3C show an example of a worn article produced by the production method described above.

As shown in FIGS. 3B and 3C, the separate sheets W1 and W2 are placed so that the tip portions Wf of the protruding portions W1u and W2u thereof partially overlap with each other.

The worn article may be subjected to various processes. For example, a plurality of elastic members Fw different from the leg elastic members F may be placed in the waist portion, the hip portion, etc., of the separate sheets W1 and W2, as shown in FIGS. 3A and 3C. A cover sheet Sc, a top sheet St, etc., may be provided. The separate sheets W1 and W2 may be folded back so that the side edge portions W1s and W2s thereof are laid on opposite end portions of the core portion C.

Figure 4A:
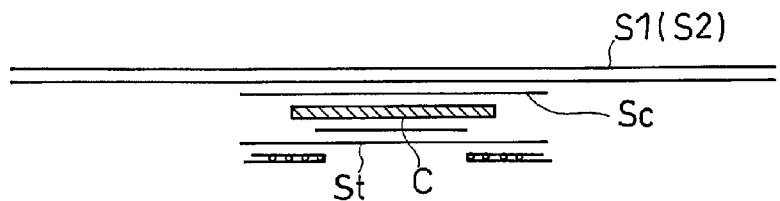
FIG. 4A is a schematic cross-sectional view showing another example of a worn article produced by the present production method.
Figure 4B:
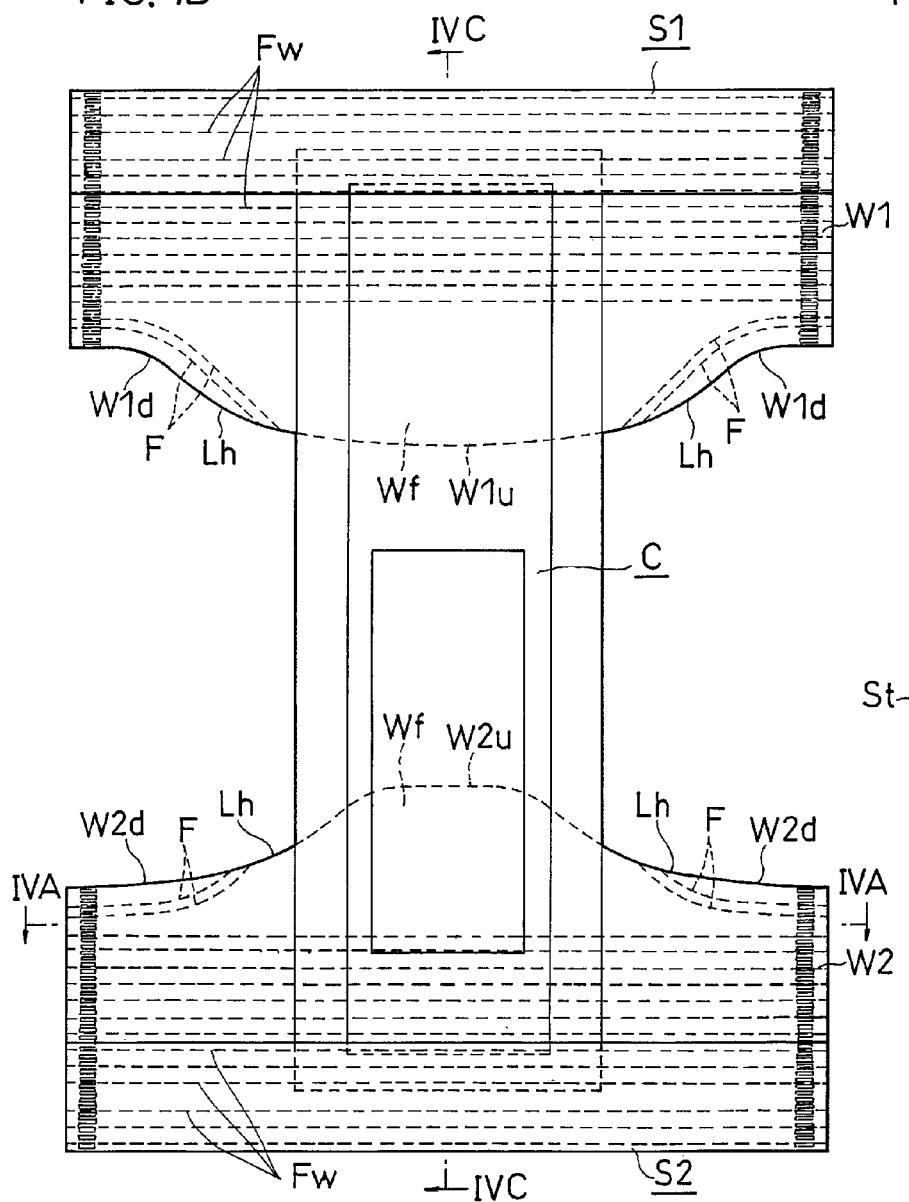
FIG. 4B is a schematic plan view thereof.
Figure 4C:
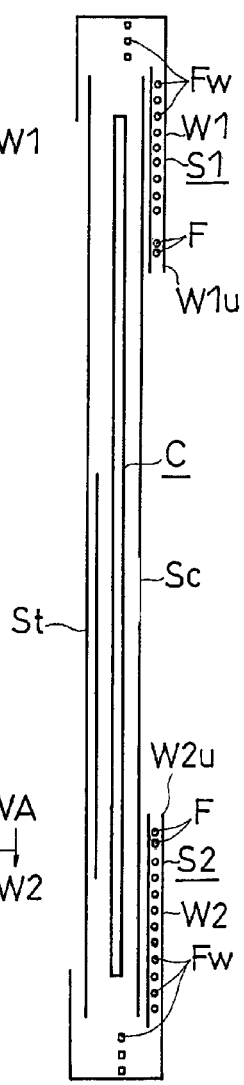
FIG. 4C is a schematic side view thereof.

The separate sheets W1 and W2 may be placed with no overlap therebetween as shown in FIGS. 4A, 4B and 4C. Such an arrangement of the separate sheets W1 and W2 may be realized by increasing the distance d1 (FIG. 1C) from the side edge portion of one separate sheet to the side edge portion of the other separate sheet in the interval-increasing step described above. The core portion C is placed so that the end portions thereof are on a pair of the separate sheets W1 and W2.

The waveforms α and β may each be such a waveform that the adjacent protruding and depressed portions within one wavelength are asymmetric with each other. Specifically, the waveforms α and β may be such that a protruding portion to be the back portion has a greater width and a protruding portion to be the front portion has a smaller width. Then, the area of the back portion, which will cover the buttocks, is increased, thus giving the wearer a sense of security.

INDUSTRIAL APPLICABILITY

The present invention is applicable to the production of a worn article having an absorbent body.

The invention claimed is:

1. A method for producing a worn article, including a first torso portion covering a part of a torso of a wearer, a second torso portion covering another portion of the torso of the wearer, and a core portion covering a crotch of the wearer, the method comprising the steps of:

carrying a strip-shaped web being continuous in a carrying direction and having a first side edge portion and a second side edge portion;

placing a leg elastic member along a first waveform on the web being carried, the first waveform being continuous in a longitudinal direction of the web and having a predetermined wavelength and a predetermined first amplitude, thereby producing a composite sheet;

cutting off the composite sheet being carried, along a cut-off line having a second waveform being continuous in the longitudinal direction of the composite sheet, having a wavelength equal to the predetermined wavelength and a second amplitude smaller than the first amplitude, and being in synchronism with the first waveform, thereby dividing the composite sheet into a first separate sheet including the first side edge portion and having first depressed portions and first protruding portions alternating each other along the cut-off line and a second separate sheet including the second side edge portion and having second protruding portions and second depressed portions alternating each other along the cut-off line, and cutting off the elastic member so that the elastic member is included in the first and second depressed portions and is excluded from tip portions of the first and second protruding portions;

shifting a phase of the first separate sheet and a phase of the second separate sheet from each other in a flow direction so that the first protruding portions and the second protruding portions face each other; and placing the core portion so as to bridge between the first protruding portions and the second protruding portions.

2. A method for producing a worn article according to claim 1, further comprising the step of relatively moving the two separate sheets in a width direction perpendicular to the longitudinal direction so as to increase a width from the first side edge portion to the second side edge portion.

3. A method for producing a worn article according to claim 2, wherein the relative movement and the phase shifting step are performed so that a part of the first protruding portion and a part of the second protruding portion overlap with each other.

4. A method for producing a worn article according to claim 2, wherein the relative movement and the phase shifting step are performed so that the first protruding portion and the second protruding portion do not overlap with each other.

* * * * *